United States Patent
Nettekoven et al.

(10) Patent No.: US 7,538,101 B2
(45) Date of Patent: May 26, 2009

(54) 1,1-DIOXO-THIOMORPHOLINYL INDOLYL METHANONE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Rosa Maria Rodriguez Sarmiento, Basel (CH); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 93 days.

(21) Appl. No.: 11/605,005

(22) Filed: Nov. 28, 2006

(65) Prior Publication Data

US 2007/0123526 A1    May 31, 2007

(30) Foreign Application Priority Data

Nov. 30, 2005    (EP)    ................... 05111479

(51) Int. Cl.
| | | |
|---|---|---|
| A01N 43/00 | (2006.01) | |
| A61K 31/54 | (2006.01) | |
| A61K 31/55 | (2006.01) | |
| C07D 223/00 | (2006.01) | |
| C07D 279/00 | (2006.01) | |
| C07D 285/00 | (2006.01) | |
| C07D 295/00 | (2006.01) | |

(52) U.S. Cl. .............................. 514/212.01; 514/222.2; 540/484; 544/3

(58) Field of Classification Search ........................ None
See application file for complete search history.

(56) References Cited

U.S. PATENT DOCUMENTS

| | | | |
|---|---|---|---|
| 4,598,089 A | 7/1986 | Hadvary et al. | |
| 4,931,463 A | 6/1990 | Barbier et al. | |
| 4,983,746 A | 1/1991 | Barbier et al. | |
| 5,175,186 A | 12/1992 | Barbier et al. | |
| 5,246,960 A | 9/1993 | Barbier et al. | |
| 5,338,755 A * | 8/1994 | Wagnon et al. | 514/414 |
| 5,399,720 A | 3/1995 | Karpf et al. | |
| 6,004,996 A | 12/1999 | Shah et al. | |

FOREIGN PATENT DOCUMENTS

| | | |
|---|---|---|
| EP | 0 189 577 | 12/1989 |
| EP | 0 185 359 | 12/1991 |
| EP | 0 524 495 | 10/1996 |
| EP | 0 443 449 | 5/1997 |
| EP | 0 978 512 | 2/2000 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 02/072548 | 9/2002 |
| WO | WO 2005/123716 | 12/2005 |

OTHER PUBLICATIONS

Berlin et al. Expert Opinion on Therapeutic Patents, 2007, 17(6), 675-87.*
Berman et al., Journal of the American Medical Association, 2008, 300(4), 433-35.*
How to prevent or delay diabetes:, http://www.diabetes.org/diabetes-prevention/how-to-prevent-diabetes.jsp, accessed Jul. 25, 2008.*
Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrick, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
Mederski, W. W. K. R.; Lefort, M.; Germann, M. Kux, D. Tetrahedron 1999 55 12757.
Watanabe, M; Nishiyama, M.; Yamamoto, T.; Koie, Y, Tetrahedron Letters 2000, 41, 481.
Old, D. W.; Harris, M. C.; Buchwald, S. L 2000 2 10 1403.
Klapars, A.; Antilla, J. C.; Huang, X.; Buchwald, S. L. J. Am. Chem. Soc. 2001 123 7727.
Takahashi, K, Tokita, S., Kotani, H. (2003) J. Pharmacol. Exp. Therapeutics 307, 213-218.
Cheng, Y, Prusoff, WH (1973) Biochem Pharmacol 22, 3099-3108.

* cited by examiner

*Primary Examiner*—James O Wilson
*Assistant Examiner*—Noble Jarrell
(74) *Attorney, Agent, or Firm*—George W. Johnston; Dennis P. Tramaloni; Samuel H. Megerditchian

(57) ABSTRACT

The present invention relates to compounds of formula I

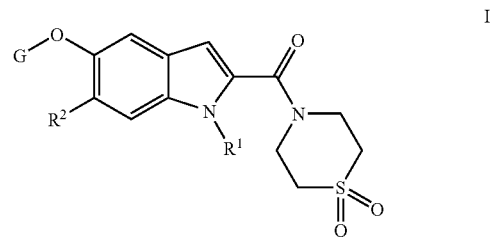

wherein $R^1$, $R^2$ and G are as defined in the description and claims and pharmaceutically acceptable salts thereof. The compounds are useful for the treatment and/or prevention of diseases which are associated with the modulation of H3 receptors.

19 Claims, No Drawings

1,1-DIOXO-THIOMORPHOLINYL INDOLYL METHANONE DERIVATIVES

PRIORITY TO RELATED APPLICATIONS

This application claims the benefit of European Application No. 05111479.1, filed Nov. 30, 2005, which is hereby incorporated by reference in its entirety.

FIELD OF THE INVENTION

The present invention is directed to novel 1,1-dioxo-thiomorpholinyl indolyl methanone derivatives, their manufacture, pharmaceutical compositions containing them and their use as medicaments. The active compounds of the present invention are useful in treating obesity and other disorders.

In particular, the present invention is directed to compounds of the general formula

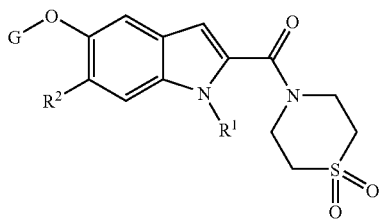

I and pharmaceutically acceptable salts thereof.

All documents cited or relied upon below are expressly incorporated herein by reference.

BACKGROUND

The compounds of formula I are antagonists and/or inverse agonists at the histamine 3 receptor (H3 receptor).

Histamine (2-(4-imidazolyl) ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2, H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

A need exists, therefore, for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In one embodiment of the present invention, provided is a compound of formula I,

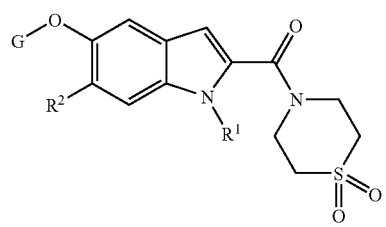

I wherein:
R$^1$ is selected from the group consisting of hydrogen, lower alkyl, lower hydroxyalkyl, lower alkoxyalkyl, lower halogenoalkyl, lower cycloalkylalkyl, lower alkanoyl, lower alkoxycarbonyl, lower cyanoalkyl, lower alkylsulfonyl, phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;

phenyl unsubstituted or substituted with one or two groups independently selected from lower alkyl, halogen, cyano, lower halogenoalkyl, lower alkoxy, lower halogenoalkoxy and lower hydroxyalkyl;

lower phenylalkyl, wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy and cyano;

$R^2$ is hydrogen or halogen;

G is a group selected from

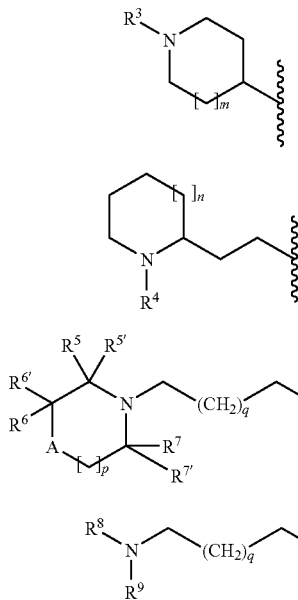

wherein m is 0, 1 or 2;

$R^3$ is selected from lower alkyl, lower halogenoalkyl, cycloalkyl, halogenocycloalkyl, lower cycloalkylalkyl and lower phenylalkyl;

n is 0, 1 or 2;

$R^4$ is lower alkyl;

p is 0, 1 or 2;

q is 0, 1 or 2;

A is selected from $CR^{10}R^{10'}$, O and S;

$R^5, R^{5'}, R^6, R^{6'}, R^7, R^{7'}, R^{10}$ and $R^{10'}$ independently from each other are selected from the group consisting of hydrogen, lower alkyl, hydoxy, halogen and dialkylamino, or $R^6$ and $R^{10}$ together form a double bond;

$R^8$ is lower alkyl;

$R^9$ is $C_3$-$C_6$-alkyl;

and pharmaceutically acceptable salts thereof.

In another embodiment of the present invention, provided is a process for the manufacture of compounds according to formula I, comprising the step of:

reacting a compound of formula II

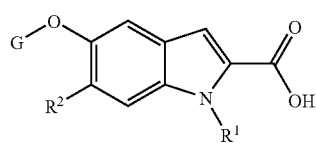

or a salt thereof, wherein $R^1$ and $R^2$ are as defined for formula I, with the amine of the formula III

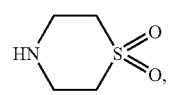

to obtain a compound of the formula I

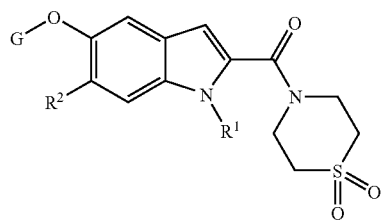

wherein $R^1$, $R^2$ and G are as defined above, and if desired, converting the compound obtained into a pharmaceutically acceptable acid addition salt.

In a further embodiment of the present invention, provided is a pharmaceutical composition, comprising a therapeutically effective amount of a compound according to formula I as well as a pharmaceutically acceptable carrier and/or adjuvant.

In a still another embodiment of the present invention, provided is a method for the treatment and/or prevention of diseases which are associated with the modulation of H3 receptors, comprising the step of administering a therapeutically active amount of a compound according to formula I to a human being or animal in need thereof.

In a still further embodiment of the present invention, provided is a method for the treatment or prevention of obesity in a human being or animal, comprising the step of administering a therapeutically effective amount of a compound according to formula I in combination or association with a therapeutically effective amount of a compound selected from the group consisting of a lipase inhibitor, an anorectic agent, a selective serotonin reuptake inhibitor and an agent that stimulates metabolism of body fat, to said human being or animal in need thereof.

In a yet another embodiment of the present invention, provided is a method of treatment or prevention of type II diabetes in a human being or animal, comprising the step of administering a therapeutically effective amount of a compound according to claim 1 in combination or association with a therapeutically effective amount of an anti-diabetic agent to said human being or animal in need thereof.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_{2-8}$-alkenyl", alone or in combination, signifies a straight-chain or branched hydrocarbon radical comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkynyl" or "$C_{2-8}$-alkynyl", alone or in combination, signifies a straight-chain or branched hydrocarbon residue comprising a triple bond and up to 8, preferably up to 6, particularly preferred up to 4 carbon atoms. Examples of alkynyl groups are ethinyl, 1-propinyl, or 2-propinyl. A preferred example is 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclopentyl and cyclohexyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfanyl" or "$C_{1-8}$-alkylsulfanyl" refers to the group R'—S—, wherein R' is lower alkyl and the term "lower alkyl" has the previously given significance. Examples of alkylsulfanyl groups are e.g. methylsulfanyl or ethylsulfanyl.

The term "lower alkylsulfanylalkyl" or "$C_{1-8}$-alkylsulfanyl-$C_{1-8}$-alkyl" refers to lower alkyl groups as defined above wherein at least one of the hydrogen atoms of the lower alkyl groups is replaced by an alkylsulfanyl group, preferably methylsulfanyl. An example for a preferred lower alkylsulfanylalkyl group is 2-methylsulfanylethyl.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenoalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenoalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower dialkylaminoalkyl" or "$C_{1-8}$-dialkylamino-$C_{1-8}$-alkyl" refers to lower alkyl groups as defined above wherein at least one of the hydrogen atoms of the lower alkyl group is replaced by a dialkylamino group, preferably dimethylamino. A preferred lower dialkylaminoalkyl group is 3-dimethylaminopropyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "lower alkoxycarbonyl" or "$C_{1-8}$-alkoxycarbonyl" refers to the group —COOR', wherein R' is lower alkyl and the term "lower alkyl" has the previously given significance. Preferred is a group —COOR', wherein R' is methyl.

The term "carbamoyl" refers to the group —CO—NH$_2$.

The term "dialkylcarbamoyl" or "$C_{1-8}$-dialkylcarbamoyl" refers to the group —CO—NR'R" wherein R' and R" are lower alkyl and the term "lower alkyl" has the previously given significance. A preferred dialkylcarbamoyl group is dimethylcarbamoyl.

The term "lower dialkylcarbamoylalkyl" or "$C_{1-8}$-dialkylcarbamoyl-$C_{1-8}$-alkyl" refers to lower alkyl groups as defined above wherein at least one of the hydrogen atoms of the lower alkyl group is replaced by a dialkylcarbamoyl group as defined herein before. A preferred lower dialkylcarbamoylalkyl groups is dimethylcarbamoylmethyl.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are furyl and pyridyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl and thiomorpholinyl. A preferred heterocyclyl group is piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers".

Stereoisomers that are not mirror images of one another are termed "diastereoisomers" and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

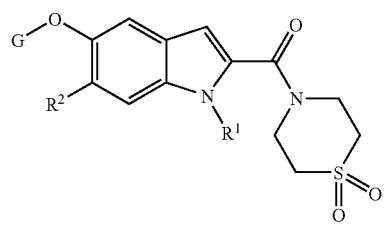

I wherein $R^1$ is selected from the group consisting of hydrogen, lower alkyl, lower hydroxyalkyl, lower alkoxyalkyl, lower halogenoalkyl, lower cycloalkylalkyl, lower alkanoyl, lower alkoxycarbonyl, lower cyanoalkyl, lower alkylsulfonyl, phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;

phenyl unsubstituted or substituted with one or two groups independently selected from lower alkyl, halogen, cyano, lower halogenoalkyl, lower alkoxy, lower halogenoalkoxy and lower hydroxyalkyl;

lower phenylalkyl, wherein the phenyl ring may be unsubstituted or substituted with one or two groups independently selected from lower alkyl, halogen, cyano, lower halogenoallyl, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy and cyano;

$R^2$ is hydrogen or halogen;

G is a group selected from

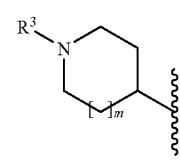

G1

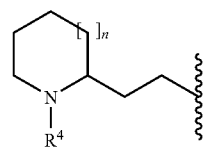

G2

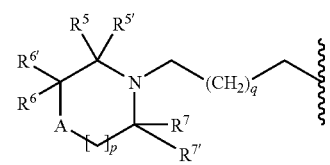

G3 and

-continued

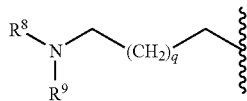
G4 wherein
m is 0, 1 or 2;
R³ is selected from lower alkyl, lower halogenoalkyl, cycloalkyl, halogenocycloalkyl, lower cycloalkylalkyl and lower phenylalkyl;
n is 0, 1 or 2;
R⁴ is lower alkyl;
p is 0, 1 or 2;
q is 0, 1 or 2;
A is selected from $CR^{10}R^{10'}$, O and S;
$R^5, R^{5'}, R^6, R^{6'}, R^7, R^{7'}, R^{10}$ and $R^{10'}$ independently from each other are selected from the group consisting of hydrogen, lower alkyl, hydoxy, halogen and dialkylamino, or
$R^6$ and $R^{10}$ together form a double bond;
$R^8$ is lower alkyl;
$R^9$ is $C_3$-$C_6$-alkyl;

and pharmaceutically acceptable salts thereof.

Furthermore, compounds of formula I according to the present invention are preferred, wherein $R^1$ is selected from the group consisting of hydrogen, lower alkyl, lower hydroxyalkyl, lower alkoxyalkyl, lower halogenoalkyl, lower cycloalkylalkyl, lower cyanoalkyl, lower alkylsulfonyl and phenyl unsubstituted or substituted with one or two groups independently selected from lower alkyl, halogen, cyano, lower halogenoalkyl, lower alkoxy, lower halogenoalkoxy and lower hydroxyalkyl.

More preferred are those compounds of formula I, wherein $R^1$ is selected from the group consisting of hydrogen, lower alkyl and lower halogenoalkyl, with those compounds, wherein $R^1$ is hydrogen, or those compounds, wherein $R^1$ is lower halogenoalkyl, being especially preferred. Most preferably, $R^1$ is trifluoroethyl.

Further preferred compounds of formula I are those, wherein $R^1$ is lower cyanoalkyl. Especially preferred is 1-cyanoethyl(propionitrile).

Also preferred are compounds of formula I of the present invention, wherein R1 is lower hydroxyalkyl or lower alkoxyalkyl. More preferably, $R^1$ is selected from the group consisting of 2-hydroxyethyl, 3-hydroxypropyl, 2-methoxyethyl and 3-methoxypropyl.

Furthermore, compounds of formula I of the present invention are preferred, wherein $R^1$ is heteroaryl unsubstituted or substituted with one or two groups independently selected from lower alkyl, lower alkoxy, halogen, lower halogenoalkyl, lower halogenoalkoxy and cyano. Most preferably, heteroaryl is pyridyl or pyrimidinyl.

$R^2$ is hydrogen or halogen. Compounds of formula I, wherein $R^2$ is selected from the group consisting of hydrogen, chloro and bromo, are preferred.

Especially preferred compounds of formula I according to the invention are those, wherein $R^2$ is hydrogen.

Furthermore, compounds of formula I according to the present invention are preferred, wherein G signifies

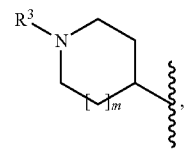
G1 wherein m is 0, 1 or 2 and $R^3$ is selected from lower alkyl, lower halogenoalkyl, cycloalkyl, halogenocycloalkyl, lower cycloalkylalkyl and lower phenylalkyl.

Within this group, those compounds of formula I are preferred, wherein $R^3$ is lower alkyl. Most preferably, $R^3$ is isopropyl.

Preferred are those compounds of formula I, wherein m is 1, thus meaning compounds, wherein G1 is represented by a piperidinyl group.

Also preferred are compounds of formula I, wherein m is 0, thus meaning compounds, wherein G1 is represented by a pyrrolidinyl group.

Furthermore, compounds of formula I according to the present invention are preferred, wherein G signifies

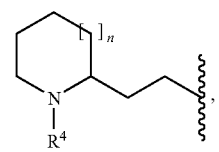
G2 wherein n is 0, 1 or 2 and $R^4$ is lower alkyl.

Also preferred are compounds of formula I according to the invention, wherein G signifies

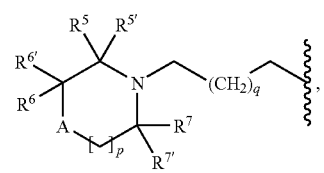
G3 wherein p is 0, 1 or 2, q is 0, 1 or 2; A is selected from $CR^{10}R^{10'}$, O and S; and
$R^5, R^{5'}, R^6, R^{6'}, R^7, R^{7'}, R^{10}$ and $R^{10'}$ independently from each other are selected from the group consisting of hydrogen, lower alkyl, hydoxy, halogen and dialkylamino, or
$R^6$ and $R^{10}$ together form a double bond.

In addition, compounds of formula I according to the present invention are preferred, wherein G signifies

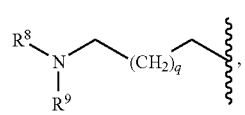
G4 wherein q is 0, 1 or 2, $R^8$ is lower alkyl and $R^9$ is lower alkyl.

Particularly preferred compounds of formula I of the present invention are the following:

(1,1-dioxo-thiomorpholin-4-yl)-[5-(1-isopropyl-piperidin-4-yloxy)-1-(2,2,2-trifluoro-ethyl)-1H-indol-2-yl]-methanone, (1,1-dioxo-thiomorpholin-4-yl)-[5-(1-isopropyl-piperidin-4-yloxy)-1H-indol-2-yl]-methanone, (1,1-dioxo-thiomorpholin-4-yl)-[1-isopropyl-5-(1-isopropyl-piperidin-4-yloxy)-1H-indol-2-yl]-methanone, (1,1-dioxo-thiomorpholin-4-yl)-[5-(1-isopropyl-pyrrolidin-3S-yloxy)-1H-indol-2-yl]-methanone, 5-[2-(1,1-dioxo-1$\lambda^6$-thiomorpholine-4-carbonyl)-5-( -isopropyl-piperidin-4-yloxy)-indol-1-yl]-pyridine-2-carbonitrile,

[6-bromo-5-(1-isopropyl-piperidin-4-yloxy)-1H-indol-2-yl]-(1,1-dioxo-1$\lambda^6$-thiomorpholin-4-yl)-methanone,

[6-bromo-1-isopropyl-5-(1-isopropyl-piperidin-4-yloxy)-1H-indol-2-yl]-(1,1-dioxo-1$\lambda^6$-thiomorpholin-4-yl)-methanone,

[6-bromo-5-(1-isopropyl-piperidin-4-yloxy)-1-(2,2,2-trifluoro-ethyl)-1H-indol-2-yl]-(1,1-dioxo-1$\lambda^6$-thiomorpholin-4-yl)-methanone,

[6-bromo-1-(2-chloro-pyridin-4-yl)-5-(1-isopropyl-piperidin-4-yloxy)-1H-indol-2-yl]-(1,1-dioxo-1$\lambda^6$-thiomorpholin-4-yl)-methanone, (1,1-dioxo-1$\lambda^6$-thiomorpholin-4-yl)-[5-(1-isopropyl-piperidin-4-yloxy)-1-(3-trifluoromethyl-phenyl)-1H-indol-2-yl]-methanone,

[1-(2-chloro-pyridin-4-yl)-5-(1-isopropyl-piperidin-4-yloxy)-1H-indol-2-yl]-(1,1-diaxo-1$\lambda^6$-thiomorpholin-4-yl)-methanone, 2-[2-(1,1-dioxo-1$\lambda^6$-thiomorpholine-4-carbonyl)-5-(1-isopropyl-piperidin-4-yloxy)-indol-1-yl]-propionitrile, (1,1-dioxo-1$\lambda^6$-thiomorpholin-4-yl)-[5-(1-isopropyl-piperidin-4-yloxy)-1-pyrimidin-5-yl-1H-indol-2-yl]-methanone,

[6-bromo-5-(1-isopropyl-piperidin-4-yloxy)-1-(2-methoxy-ethyl)-1H-indol-2-yl]-(1,1-dioxo-1$\lambda^6$-thiomorpholin-4-yl)-methanone,

[6-bromo-5-(1-isopropyl-piperidin-4-yloxy)-1-(3-methoxy-propyl)-1H-indol-2-yl]-(1,1-dioxo-1$\lambda^6$-thiomorpholin-4-yl)-methanone,

[6-bromo-1-(2-hydroxy-ethyl)-5-(1-isopropyl-piperidin-4-yloxy)-1H-indol-2-yl]-(1,1-dioxo-1$\lambda^6$-thiomorpholin-4-yl)-methanone,

[6-bromo-1-(3-hydroxy-propyl)-5-(1-isopropyl-piperidin-4-yloxy)-1H-indol-2-yl]-(1,1-Dioxo-1$\lambda^6$-thiomorpholin-4-yl)-methanone, (S)-2-[2-(1,1-dioxo-1$\lambda^6$-thiomorpholine-4-carbonyl)-5-(1-isopropyl-piperidin-4-yloxy)-indol-1-yl]-propionitrile, (R)-2-[2-(1,1-dioxo-1$\lambda^6$-thiomorpholine-4-carbonyl)-5-(1-isopropyl-piperidin-4-yloxy)-indol-1-yl]-propionitrile,

[5-(1-cyclobutyl-piperidin-4-yloxy)-1-isopropyl-1H-indol-2-yl]-(1,1-dioxo-1$\lambda^6$-thiomorpholin-4-yl)-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises b) reacting a compound of formula II

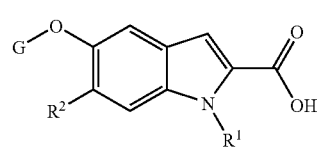

or a salt thereof, wherein $R^1$ and $R^2$ are as defined herein before, with the amine of the formula III

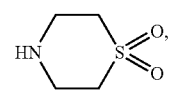

to obtain a compound of the formula I

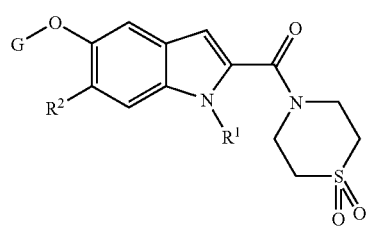

wherein $R^1$, $R^2$ and G are as defined herein before, and if desired, converting the compound obtained into a pharmaceutically acceptable acid addition salt.

The term a salt of a compound of formula II embraces all acid addition salts with acids, for example hydrochloride, hydrobromide, phosphate, acetate, fumarate, maleate, salicylate, sulphate, pyruvate, citrate, lactate, mandelate, tartrate and methanesulphonate. Preferred are the hydrochloride salts. In addition, these hydrochloric salts may contain an equivalent of an alkali chloride salt, such as lithium chloride, sodium chloride or potassium chloride.

In more detail, the compounds of formula I can be manufactured by the methods given below, by the methods given in the examples or by analogous methods. The preparation of compounds of formula I of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

Compounds of general formula I can be prepared according to scheme 1 as follows:

The syntheses of ethers are widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The transformation can be affected by employing reaction conditions which are commonly utilised in the so called "*Mitsunobu reaction*" which is known to those in the art and widely described (Hughes, David L. The Mitsunobu reaction. Organic Reactions, New York, 1992 42 335-656.) We find it convenient to couple a phenolic alcohol IV with alcohols HO-G VI (either commercially available or accessible by methods described in references or by methods known in the art, as appropriate) under conditions employing a phosphine such as tributylphosphine or triphenylphosphine and the like and a diazo-compound like diethyl-azodicarboxylate, diiso-

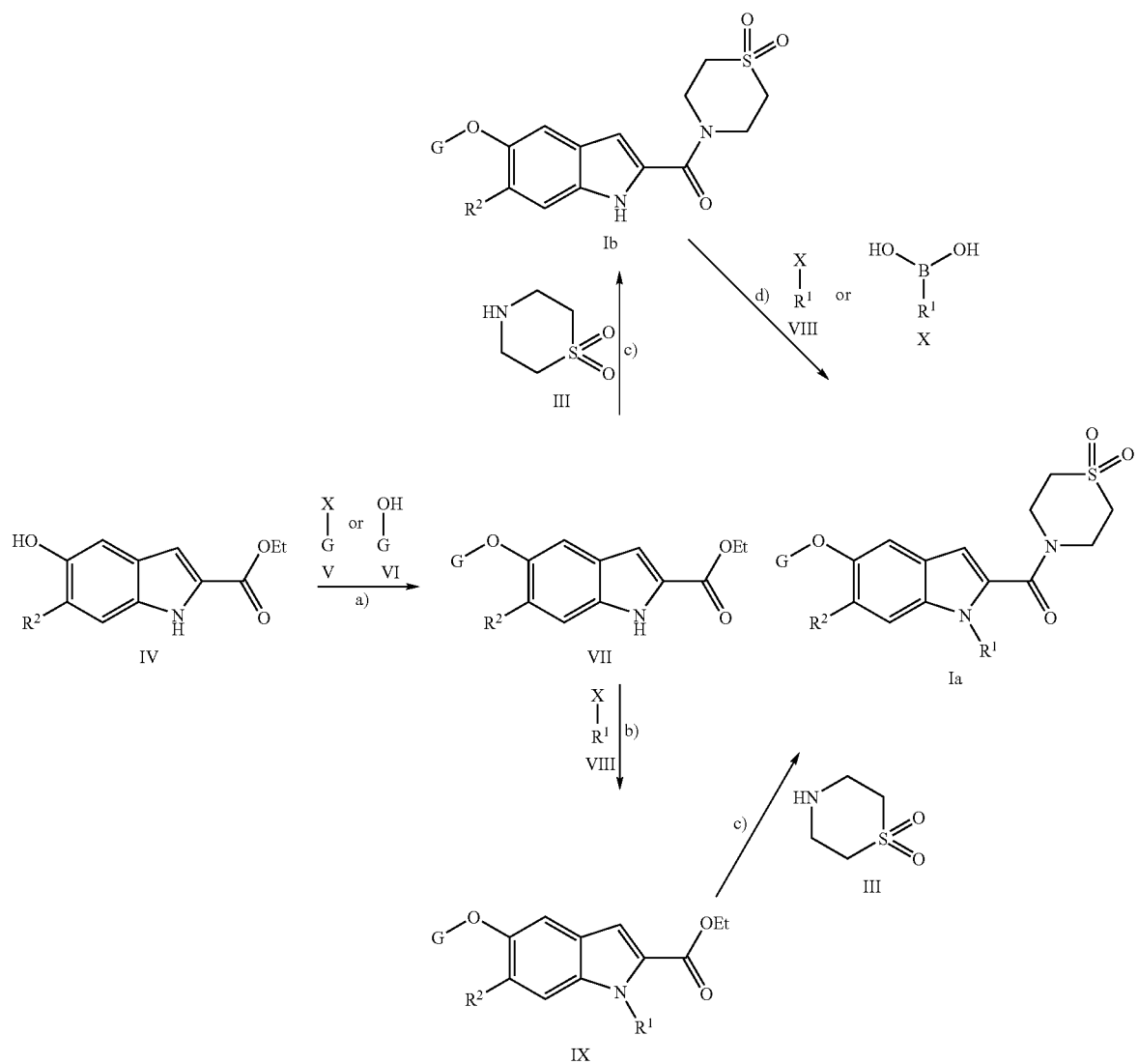

propyl-azodicarboxylate (optionally polymer bound), di-tert-butylazodicarboxylate, tetramethyl azodicarboxamide and the like in a solvent commonly used in such transformations like tetrahydrofuran, toluene, dichloromethane and the like. There is no particular restriction on the nature of the solvent to be employed, provided that it has no adverse effect on the reaction or the reagents involved and that it can dissolve the reagents, at least to some extent. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the compounds of formula VII.

Alternatively, compounds of formula IV can be subjected to a reaction in which the phenolic OH will substituted by G-X V (either commercially available or accessible by methods described in references or by methods known in the art, as appropriate). Conditions commonly used in such types of transformation are widely described in literature and known to those in the art. The leaving group X can be any halogen group or pseudo halogen (e.g. trifluoromethylmethanesulfonyl, para-toluenesulfonyl, methanesulfonyl and the like). The reaction might be carried out in the presence or absence of a solvent and preferably in the presence of a base. Solvents like N,N-dimethylformamide, N,N-dimethyl acetamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, N-ethyldiisopropylamine, sodium carbonate and cesium carbonate and the like. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds VII.

Compounds VII can be subjected to a reaction in which the indole NH will be substituted by lower alkyl substituents, benzyl substituents, alkyl, alkanoyl and arylsulfonyl substituent, e.g. through a reaction with an alkylating, acylating or sulfonylating agent (either commercially available or accessible by methods described in references or by methods known in the art, as appropriate). Typical examples of an alkylating or acylating agent VIII are methyl iodide, 2-bromopropane, 2,2,2-trifluoroethyl-methanesulfonate, methanesulfonylchloride or phenylsulfonylchloride. Conditions commonly used in such types of transformation are widely described in literature and known to those in the art. X signifies a leaving group such as any halogen group (chlorine, bromine, iodine) or pseudo halogens group (e.g. trifluoromethylmethanesulfonyl, paratoluensulfonyl, methanesulfonyl and the like). The reaction might be carried out in the presence or absence of a solvent and preferably in the presence of a base. Solvents like N,N-dimethylformamide, N,N-dimethyl acetamide, tetrahydrofuran, diethyl ether, dioxane, acetonitrile, butanone and the like are conveniently used. There is no particular restriction on the nature of the solvent to be employed, provided that it has no adverse effect on the reaction or the reagents involved and that it can dissolve the reagents, at least to some extent. Usually the reaction is carried out in the presence of a base. Suitable bases include sodium hydride, N-ethyldiisopropylamine, sodium carbonate and cesium carbonate and the like. The reaction can take place over a wide range of temperatures and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds IX.

The compounds of formula IX are transformed into the free acids under basic conditions, for example by using lithium hydroxide monohydrate as a base. The free acid or any of its suitable salt is coupled to thiomorpholine-1,1-dioxide (purchased at Syntec, ref M1201) by the procedures known to those in the art (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). We found it convenient to use 2-(1H-benzotriazole-1-yl)-1,1,3,3-tetramethyluronium tetrafluoroborate and diisopropylethylamine in dimethylformamide, yielding a compound of formula Ia.

The indoles Ib might be the desired products, however, they might optionally be subjected to a subsequent alkylating reaction as described above under point b) to furnish the desired compounds Ia.

Alternatively, compound Ib can be alkylated or arylated by a boronic acid or a boronic ester of formula X (either commercially available or accessible by methods described in references or by methods known in the art, as appropriate). Conditions commonly used in such types of transformation are described in literature and known to those in the art (e.g. Mederski, W. W. K. R.; Lefort, M.; Germann, M. Kux, D. Tetrahedron 1999 55 12757). $R^1$ can be any aryl, cycloalkyl or heteroaryl compounds.

Alternatively, compound Ib can be arylated by compound of general formula $R^1$—X (either commercially available or accessible by methods described in references or by methods known in the art, as appropriate). The transformation can be affected by employing reaction conditions which are known to those in the art and widely described (e.g. Watanabe, M; Nishiyama, M.; Yamamoto, T.; Koie, Y, Tetrahedron Letters 2000, 41, 481; Old, D. W.; Harris, M. C.; Buchwald, S. L 2000 2 10 1403; Kiapars, A.; Antilla, J. C.; Huang, X.; Buchwald, S. L. J. Am. Chem. Soc. 2001 123 7727). The leaving group X can be any halogen group (chlorine, bromine, iodine) or pseudo halogen group (e.g. trifluoromethylmethanesulfonyl, paratoluensulfonyl, methanesulfonyl and the like) and $R^1$ can be any aryl or heteroaryl groups.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X) and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449 and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia) and the like; 2) biguanides such as metformin (glucophage) and the like; 3) sulfonylureas such as glibenclamide, glimepiride (amaryl), glipizide (glucotrol), glyburide (DiaBeta) and the like; 4) nonsulfonylureas such as nateglinide (starlix), repaglimide (prandin) and the like; 5) PPARα/γ agonists such as GW-2331 and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1 and the like; 8) α-Glucosidase inhibitors such as acarbose (precose) or miglitol (glyset) and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid) and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe and the like; 4) CETP inhibitors such as torcetrapib, JTT 705 and the like; 5) PPARα-agonists such as beclofibrate, gemfibrozil (lopid), fenofibrate (lipidil), bezafibrate (bezalip) and the like; 6) lipoprotein synthesis inhibitors such as niacin and the like; and 7) niacin receptor agonists such as nicotinic acid and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik) and the like; 2) Angiotensin II Receptor Antagonists including candesartan (atacand), eprosartan (teveten), irbesartan (avapro), losartan (cozaar), telmisartan (micadisc), valsartan (diovan) and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne) and the like; alpha-1 adrenergic blockers including prazosin (minipress), doxazosin (cardura), terazosin (hytrin), phenoxybenzamine (dibenzyline) and the like; peripheral adrenergic-neuronal blockers including guanadrel (hylorel), guanethidine (ismelin), reserpine (serpasil) and the like; alpha-2 adrenergic blockers including a-methyldopa (aldomet), clonidine (catapres), guanabenz (wytensin), guanfacine (tenex) and the like; 4) Blood Vessel Dilators (Vasodilators) including hydralazine (apresoline), minoxidil (lonitren), clonidine (catapres) and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil) and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox) and the like; loop diuretics, such as bumetanide (bumex) and furosemide (lasix), ethacrynic acid (edecrin), torsemide (demadex) and the like; potassium-sparing diuretics including amiloride (midamor), triamterene (dyrenium), spironolactone (aldactone) and the tiamenidine (symcor) and the like; 7) Tyrosine Hydroxylase Inhibitors, including metyrosine (demser) and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165 and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H—(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3H(R)$α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of $[^3H]$-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 0.1 nM to about 1000 nM, preferably of about 0.1 nM to about 300 nM and more preferably of about 0.1 nM to about 100 nM. The following table shows measured values for some selected compounds of the present invention.

The following table shows measured values for some selected compounds of the present invention.

|  | $K_i$ (nM) |
| --- | --- |
| Example 1 | 3 |
| Example 4 | 49 |

Demonstration of additional biological activities of the compounds of the present invention may be accomplished through in vitro, ex vivo and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAI mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein and serum triglyceride levels are determined.

Method for Measuring HDL-Cholesterol Levels

To determine plasma HDL-cholesterol levels, hApoAI mice are bled and grouped with equivalent mean plasma HDL-cholesterol levels. The mice are orally dosed once daily with vehicle or test compound for 7 to 14 days and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable salts and esters, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediate 1

5-(1-Isopropyl-piperidin-4-yloxy)-1H-indole-2-carboxylic acid ethyl ester

Step 1: 1-Isopropyl-piperidin-4-ol

To a cold (0° C.) solution of 1-isopropylpiperidone (purchased at Chemie Brunschwig AG, 100 g, 1.0 eq.) in ethanol (500 mL) was added sodium borohydride (19.3 g, 0.7 eq.) in small portions. The reaction mixture was allowed to warm up to room temperature and was stirred overnight. After concentration in vacuo, ice water (1 kg), sodium hydroxide aqueous solution (28% in mass, 0.5 L) and dichloromethane (1 L) were added. The mixture was stirred vigorously for 4 h and the aqueous layer was extracted with dichloromethane. Combined organic layers were washed with brine, dried over sodium sulfate, filtered and purified by fractionated vacuum distillation (20 mBar). One fraction (95° C. at 20 mBar) was isolated to yield 61.3 g (60%) of the title product as colorless oil. MS (m/e): 144.5 ($MH^+$, 100%).

Step 2: 5-(1-Isopropyl-pyrrolidin-3-yloxy)-1H-indole-2-carboxylic acid ethyl ester To a cold (0° C.) mixture of 5-hydroxy-1H-indole-2-carboxylic acid ethyl ester (10 g, 1.0 eq.), 1-isopropyl-piperidin-4-ol (intermediate 1, step 1, 7.32 g, 1.05 eq.) and triphenylphosphine (15.3 g, 1.2 eq.) in tetrahydrofuran (280 ml) was slowly added a solution of diisopropylazodicarboxylate (11.8 g, 1.2 eq.) in tetrahydrofuran (20 mL). The mixture was stirred 30 min at 0° C. and overnight at room temperature, was concentrated in vacuo, dissolved in methyltertiobutylether (310 mL), washed with sodium hydroxide aqueous solution (0.5N), brine, dried over $Na_2SO_4$, filtered and evaporated. The residue was purified on silica eluting with dichloromethane/methanol/ammoniac. One fraction was isolated and dried in vacuo, to yield 7.0 g (43%) of the desired product as white solid. MS (m/e): 331.5 ($MH^+$, 100%)

Example 1

(1,1-Dioxo-thiomorpholin-4-yl)-[5-(1-isopropyl-piperidin-4-yloxy)-1-(2,2,2-trifluoro-ethyl)-1H-indol-2-yl]-methanone Step 1: 5-(1-Isopropyl-piperidin-4-yloxy)-1-(2,2,2-trifluoro-ethyl)-1H-indole-2-carboxylic acid ethyl ester To a mixture of 5-(1-isopropyl-pyrrolidin-3-yloxy)-1H-indole-2-carboxylic acid ethyl ester (intermediate, 4 g, 1.0 eq.) in dimethylformamide (40 mL) was added sodium hydride (dispersion in oil, 60% in mass, 533 mg, 1.1 eq.) in several portions. The solution was stirred 30 min at 70° C. Then 2,2,2-trifluoroethyltrifluoromethanesulfonate (3.37 g, 1.2 eq.) was added and the reaction mixture was stirred at 70° C. overnight. The reaction mixture was partitioned between an aqueous solution of sodium hydrogenocarbonate and ethyl acetate. The organic layer was washed with water and brine, evaporated in vacuo and then purified on silica eluting with dichloromethane/methanol/ammoniac. One fraction was isolated and dried in vacuo, to yield 3.9 g (78%) of the desired product as off-white solid. MS (m/e): 413.5 ($MH^+$, 100%)

Step 2: 5-(1-Isopropyl-piperidin-4-yloxy)-1-(2,2,2-trifluoro-ethyl)-1H-indole-2-carboxylic acid hydrochloric salt with one equivalent of lithium chloride To a solution of 5-(1-isopropyl-piperidin-4-yloxy)-1-(2,2,2-trifluoro-ethyl)-1H-indole-2-carboxylic acid ethyl ester (3.9g, 1.0 eq.) in tetrahydrofuran (30 mL), water (15 mL) and methanol (7 mL) was added lithium hydroxide monohydrate (460 mg, 1.16 eq.). The reaction mixture was refluxed overnight. After concentration in vacuo the residue was acidified (pH:2) with hydrochloric acid (2N). The resulting mixture was dried in vacuo to yield 4.4 g (99%) of the desired product as off-white solid. MS (m/e): 462.5 ($M-H^-$, 100%).

Step 3: (1,1-Dioxo-thiomorpholin-4-yl)-[5-(1-isopropyl-piperidin-4-yloxy)-1-(2,2,2-trifluoro-ethyl)-1H-indol-2-yl]-methanone A mixture of 5-(1-isopropyl-piperidin-4-yloxy)-1-(2,2,2-trifluoro-ethyl)-1H-indole-2-carboxylic acid, hydrochloric salt with one equivalent of lithium chloride (650 mg, 1.0 eq.), 2-(1H-benzotriazole-1-yl)-1,1,3,3-tetramethylurunium tetrafluoroborate (563 mg, 1.2 eq.), thiomorpholine-1,1-dioxide (purchased at Syntec, ref. M1201) and diisopropylethylamine (1.22 mL, 5 eq.) in dimethylformamide was stirred at room temperature for 24 h and then partitioned between an aqueous solution of sodium hydrogenocarbonate and ethyl acetate. The aqueous layer was extracted with ethyl acetate and the combined organic layers were washed with water and brine, dried over sodium sulfate, filtered, evaporated in vacuo and purified on silica eluting with dichloromethane/methanol/ammoniac. One fraction was isolated and dried in vacuo, to yield 468 mg (66%) of the desired product as off-white solid. MS (m/e): 502.5 ($MH^+$, 100%).

Example 2

(1,1-Dioxo-thiomorpholin-4-yl)-[5-(1-isopropyl-piperidin-4-yloxy)-1H-indol-2-yl]-methanone Step 1: 5-(1-Isopropyl-piperidin-4-yloxy)-1H-indole-2-carboxylic acid hydrochloric salt with one equivalent of lithium chloride A mixture of 5-(1-isopropyl-pyrrolidin-3-yloxy)-1H-indole-2-carboxylic acid ethyl ester (intermediate 1, 1.98 g, 1.0 eq.) and lithium hydroxide monohydrate (300 mg, 1.15 mmol) in tetrahydrofuran (30 mL), methanol (30 mL) and water (15 mL) was heated to 100° C. for 2 h. The organic solvents were removed and aq. 1N HCl was added to adjust the pH of the solution in a range of 2 to 3. Subsequently, the mixture was evaporated to dryness and the mixture was used without further purification in the next step. MS (m/e): 301.5 ($M-H^-$, 100%).

Step 2: (1,1-Dioxo-thiomorpholin-4-yl)-[5-(1-isopropyl-piperidin-4-yloxy)-1H-indol-2-yl]-methanone In analogy to the procedure described for the synthesis of example 1, step 3, the title compound was synthesized from 5-(1-isopropyl-piperidin-4-yloxy)-1H-indole-2-carboxylic acid hydrochloric salt with one equivalent of lithium chloride (example 2, step 1) and thiomorpholine-1,1-dioxide (purchased at Syntec, ref. M1201). The title product was obtained in 75% yield as white solid. MS (m/e): 420.5 (MH$^+$, 100%).

Example 3

(1,1-Dioxo-thiomorpholin-4-yl)-[1-isopropyl-5-(1-isopropyl-piperidin-4-yloxy)-1H-indol-2-yl]-methanone To a mixture of (1,1-dioxo-thiomorpholin-4-yl)-[5-(1-isopropyl-piperidin-4-yloxy)-1H-indol-2-yl]-methanone (Example 2, 100 mg, 1.0 eq.) and isopropyl-methanesulfonate (67 mg, 2.0 eq.) in dimethylformamide (4 mL) was added cesium carbonate (156 mg, 2.0 eq.). The solution was stirred 22 h at 95° C. The reaction mixture was concentrated in vacuo and the residue partitioned between water and methyl-tert-butylether. The aqueous layer was extracted with methyl-tert-butylether. The combined organic layer was washed with brine, dried over sodium sulfate, filtered, concentrated in vacuo and then purified on silica, eluting with cyclohexane/ethyl acetate. One fraction was isolated and dried in vacuo, to yield 52 mg (47%) of the desired product as off-white solid. MS (m/e): 462.5 (MH$^+$, 100%)

Example 4

(1,1-Dioxo-thiomorpholin-4-yl)-[5-(1-isopropyl-pyrrolidin-3S-yloxy)-1H-indol-2-yl]-methanone Step 1: 5-((S)-1-Benzyl-pyrrolidin-3-yloxy)-1H-indole-2-carboxylic acid ethyl ester To a cold (0° C.) mixture of ethyl-5-hydroxyindole-2-carboxylate (purchased at Biosynth, H-6350, 20.5 g, 1.0 eq.), (R)-1-benzyl-3-pyrrolidinol (23 g, 1.3 eq.) and tri-n-butylphosphine (58 mL, 2.0 eq.) was slowly added 1,1'-(azodicarbonyl)dipiperidine (50.4 g, 2.0 eq.) in several portions. The reaction mixture was stirred at room temperature overnight and then filtered off. The filtrate was concentrated in vacuo and diethylether was added. The precipitate was filtered off and the filtrate was concentrated in vacuo and purified on silica eluting with dichloromethane/methanol/ammoniac. One fraction was isolated and dried in vacuo, to yield 18 mg (49%) of the desired product as light yellow foam. MS (m/e): 365.5 (MH$^+$, 100%).

Step 2: 5-((S)-1-Isopropyl-pyrrolidin-3-yloxy)-1H-indole-2-carboxylic acid ethyl ester To a mixture of 5-((S)-1-benzyl-pyrrolidin-3-yloxy)-1H-indole-2-carboxylic acid ethyl ester (18.0 g, 1.0 eq.) and acetic acid (28 mL, 10 eq.) in ethanol (500 mL) was added palladium on activated charcoal (10% in mass, 2.0 g, 0.04 eq.) and the reaction vessel was flushed with hydrogen (1 Atm). The reaction mixture was stirred 18 h at room temperature and then filtered off and concentrated in vacuo. The residue (28.4 g) was dissolved in dimethylformamide (500 mL) and potassium carbonate was added. The mixture was stirred 15 min at room temperature. Then 2-iodopropane (42 g, 5.0 eq.) was added and the mixture was stirred 4 h at 50° C. The reaction mixture was filtered off and the filtrate was evaporated in vacuo. The residue was dissolved in acetone, filtered and the filtrate was evaporated in vacuo then purified on silica eluting with dichloromethane/methanol/ammoniac. One fraction was isolated and dried in vacuo, to yield 9.3 g (59%) of the desired product as light brown solid. MS (m/e): 317.4 (MH$^+$, 100%).

Step 3: 5-((S)-1-Isopropyl-pyrrolidin-3-yloxy)-1H-indole-2-carboxylic acid hydrochloric salt with one equivalent of lithium chloride To a solution of 5-((S)-1-isopropyl-pyrrolidin-3-yloxy)-1H-indole-2-carboxylic acid ethyl ester (8.9 g, 1.0 eq.) in tetrahydrofuran (100 mL), water (50 mL) and methanol (10 mL) lithium hydroxide monohydrate (1.3 g, 1.10 eq.) was added. The reaction mixture was refluxed overnight and then concentrated in vacuo. The residue was acidified (pH: 2) with hydrochloric acid (2N). The resulting mixture was dried in vacuo yielding 10.5 g (100%) of the desired product as brown foam. MS (m/e): 287.0 (M–H$^-$, 100%).

Step 4: (1,1-Dioxo-thiomorpholin-4-yl)-[5-(1-isopropyl-pyrrolidin-3S-yloxy)-1H-indol-2-yl]-methanone In analogy to the procedure described for the synthesis of example 1, step 3, the title compound was synthesized from 5-((S)-1-isopropyl-pyrrolidin-3-yloxy)-1H-indole-2-carboxylic acid hydrochloric salt with one equivalent of lithium chloride (example 4, step 3) and thiomorpholine-1,1-dioxide (purchased at Syntec, ref. M1201). The desired product was obtained in a yield of 67% as white solid. MS (m/e): 406.5 (MH$^+$, 100%).

Example 5

5-[2-(1,1-Dioxo-1$\lambda^6$-thiomorpholine-4-carbonyl)-5-(1-isopropyl-piperidin-4-yloxy)-indol-1-yl]-pyridine-2-carbonitrile To a mixture of (1,1-dioxo-thiomorpholin-4-yl)-[5-(1-isopropyl-piperidin-4-yloxy)-1H-indol-2-yl]-methanone (Example 2, 150 mg, 1.0 eq.), anhydrous copper(II) acetate (131 mg, 2 eq.), pyridine (120 microL, 4 eq.) in dichloromethane (3.5 mL), 2-cyanopyridine-5-boronic acid pinacol ester (247 mg, 3 eq.) was added. The reaction mixture was stirred for 4 days and then concentrated in vacuo. The residue was then purified on silica eluting with dichloromethane/methanol 98:2 v:v. One fraction was isolated and dried in vacuo, to yield 57 mg (23%) of the desired product as light yellow oil. MS (m/e): 522.5 (MH$^+$, 100%).

Example 6

[6-Bromo-5-(1-isopropyl-piperidin-4-yloxy)-1H-indol-2-yl]-(1,1-dioxo-1$\lambda^6$-thiomorpholin-4-yl)-methanone Step 1: 6-Bromo-5-hydroxy-1H-indole-2-carboxylic acid ethyl ester The solution of 8.30 g (27.8 mmol) 6-bromo-5-methoxy-1H-indole-2-carboxylic acid ethyl ester (prepared according to J. Org. Chem. 1974, 39, 3580) in 160 mL dichloromethane was cooled to −78° C. At this temperature, 55.7 mL boron tribromide (55.7 mmol; 1M solution in dichloromethane)

were added. The solution was allowed to warm to room temperature and after 30 min. The solution was poured on 10% aqueous sodium bicarbonate solution, the phases were separated and the aqueous phase was extracted three times with ethyl acetate. The combined organic layers were washed with water followed by brine, dried over magnesium sulfate, filtered and evaporated. The residue was flash-chromatographed on silica gel with n-hexane: ethyl acetate (2:1 v/v) as eluant to give 5.7 g (72%) of the product as a light yellow solid. MS (m/e): 282.2 (M–H$^+$, 100%).

Step 2: 6-Bromo-5-(1-isopropyl-piperidin-4-yloxy)-1H-indole-2-carboxylic acid ethyl ester To the suspension of 0.25 g (0.88 mmol) 6-bromo-5-hydroxy-1H-indole-2-carboxylic acid ethyl ester in 5 mL tetrahydrofuran, 0.15 g (1.05 mmol) 1-isopropyl-piperidin-4-ol (commercially available) and 0.28 g (1.07 mmol) tributylphosphine were added. The suspension was cooled to 0° C., 0.244 g (1.06 mmol) di-tert-butyl azodicarboxylate was added and the reaction was allowed to reach room temperature. After 48 hours the suspension was filtered and the filtrate was evaporated. The residue was flash-chromatographed on silica gel with a gradient of dichloromethane:methanol (100:0 to 60:40 v/v) to give 0.20 g (55%) of the product as a light yellow foam. MS (m/e): 409.0 (M–H$^+$, 100%).

Step 3: 6-Bromo-5-(1-isopropyl-piperidin-4-yloxy)-1H-indole-2-carboxylic acid, hydrochloric salt in mixture with lithium chloride A mixture of 6-bromo-5-(1-isopropyl-piperidin-4-yloxy)-1H-indole-2-carboxylic acid ethyl ester (3.4 g, 1.0 eq.) and lithium hydroxide (249 mg 1.25 eq.) in a mixture of tetrahydrofuran (170 mL) and water (85 mL) was refluxed for 2 h then the volatiles where removed in vacuo and the pH was adjusted to ca. 2. The suspension was dried by azeotropic removal of water (toluol) to yield 3.95 g of the desired product as light yellow solid which was used without further purification. MS (m/e): 416.5.0 (M–H$^+$, 100%).

Step 4: [6-Bromo-5-(1-isopropyl-piperidin-4-yloxy)-1H-indol-2-yl]-(1,1-Dioxo-1$\lambda^6$-thiomorpholin-4-yl)-methanone In analogy to the procedure described for the synthesis of example 1, step 3 the title compound was synthesized from 6-Bromo-5-(1-isopropyl-piperidin-4-yloxy)-1H-indole-2-carboxylic acid, hydrochloric salt in mixture with lithium chloride (Example 6 step 3) and thiomorpholine-1,1-dioxide (purchased at Syntec, ref. M1201). The desired product was obtained in a yield of 60% as light yellow solid. MS (m/e): 499.5 (MH$^+$, 100%).

Example 7

[6-Bromo-1-isopropyl-5-(1-isopropyl-piperidin-4-yloxy)-1H-indol-2-yl]-(1,1-dioxo-1$\lambda^6$-thiomorpholin-4-yl)-methanone In analogy to the procedure described for the synthesis of example 3, the title compound was synthesized from [6-bromo-5-(1-isopropyl-piperidin-4-yloxy)-1H-indol-2-yl]-(1,1-dioxo-1$\lambda^6$-thiomorpholin-4-yl)-methanone (Example 6, step 4) and isopropylmethanesulfonate. The desired product was obtained in a yield of 69% as light yellow solid. MS (m/e): 540.3 (M+H, 100%).

Example 8

[6-Bromo-5-(1-isopropyl-piperidin-4-yloxy)-1-(2,2,2-trifluoro-ethyl)-1H-indol-2-yl]-(1,1-dioxo-1$\lambda^6$-thiomorpholin-4-yl)-methanone In analogy to the procedure described for the synthesis of example 1, step 1, the title compound was synthesized from [6-bromo-5-(1-isopropyl-piperidin-4-yloxy)-1H-indol-2-yl]-(1,1-dioxo-1$\lambda^6$-thiomorpholin-4-yl)-methanone (Example 6, step 4) and 2,2,2-trifluoroethyltrifluoromethanesulfonate. The desired product was obtained in a yield of 15% as white solid. MS (m/e): 580.1 (M+H, 100%).

Example 9

[6-Bromo-1-(2-chloro-pyridin-4-yl)-5-(1-isopropyl-piperidin-4-yloxy)-1H-indol-2-yl]-(1,1-dioxo-1$\lambda^6$-thiomorpholin-4-yl)-methanone In analogy to the procedure described for the synthesis of example 5, the title compound was synthesized from [6-bromo-5-(1-isopropyl-piperidin-4-yloxy)-1H-indol-2-yl]-(1,1-dioxo-1$\lambda^6$-thiomorpholin-4-yl)-methanone (Example 6, step 4) and 2-chloropyridine-4-boronic acid. The desired product was obtained in a yield of 7% as white solid. MS (m/e): 609.0 (M+H, 100%).

Example 10

(1,1-Dioxo-1$\lambda^6$-thiomorpholin-4-yl)-[5-(1-isopropyl-piperidin-4-yloxy)-1-(3-trifluoromethyl-phenyl)-1H-indol-2-yl]-methanone In analogy to the procedure described for the synthesis of example 5, the title compound was synthesized from (1,1-dioxo-thiomorpholin-4-yl)-[5-(1-isopropyl-piperidin-4-yloxy)-1H-indol-2-yl]-methanone (Example 2) and (3-trifluoromethyl)-phenylboronic acid. The desired product was obtained in a yield of 77% as light yellow solid. MS (m/e): 564.5 (MH$^+$, 100%).

Example 11

[1-(2-Chloro-pyridin-4-yl)-5-(1-isopropyl-piperidin-4-yloxy)-1H-indol-2-yl]-(1,1-dioxo-1$\lambda^6$-thiomorpholin-4-yl)-methanone In analogy to the procedure described for the synthesis of example 5, the title compound was synthesized from (1,1-dioxo-thiomorpholin-4-yl)-[5-(1-isopropyl-piperidin-4-yloxy)-1H-indol-2-yl]-methanone (Example 2) and 2-chloropyridine-4-boronic acid. The desired product was obtained in a yield of 8% as an off-white solid. MS (m/e): 531.5 (M$^+$, 100%).

Example 12 rac-2-[2-(1,1-Dioxo-1$\lambda^6$-thiomorpholine-4-carbonyl)-5-(1-isopropyl-piperidin-4-yloxy)-indol-1-yl]-propionitrile In analogy to the procedure described for the synthesis of example 1, step 1, the title compound was synthesized from (1,1-dioxo-thiomorpholin-4-yl)-[5-(1-isopropyl-piperidin-4-yloxy)-1H-indol-2-yl]-methanone (Example 2) and 2-bro-

Example 13

(1,1-Dioxo-1λ$^6$-thiomorpholin-4-yl)-[5-(1-isopropyl-piperidin-4-yloxy)-1-pyrimidin-5-yl-1H-indol-2-yl]-methanone To a mixture of (1,1-dioxo-thiomorpholin-4-yl)-[5-(1-isopropyl-piperidin-4-yloxy)-1H-indol-2-yl]-methanone (Example 2, 1 g, 1.0 eq.), trans-1,2-diaminocyclohexane (186 microL, 0.65 eq.), copper(I) iodide (54 mg, 0.12 eq.), potassium phosphate (1.06 g, 2.1 eq.) and potassium carbonate (692 mg, 2.1 eq.) in dioxane (20 mL) 5-bromopyrimidine (417 mg, 1.1 eq.) was added. The reaction mixture was stirred for 5 days and then concentrated in vacuo. The residue was then purified on silica eluting with dichloromethane/methanol 98:2 v:v. One fraction was isolated and dried in vacuo, to yield 158 mg (13%) of the desired product as light yellow oil. MS (m/e): 498.6 (MH$^+$, 100%).

Example 14

[6-Bromo-5-(1-isopropyl-piperidin-4-yloxy)-1-(2-methoxy-ethyl)-1H-indol-2-yl]-(1,1-dioxo-1λ$^6$-thiomorpholin-4-yl)-methanone In analogy to the procedure described for the synthesis of example 1, step 1, the title compound was synthesized from [6-bromo-5-(1-isopropyl-piperidin-4-yloxy)-1H-indol-2-yl]-(1,1-dioxo-1λ$^6$-thiomorpholin-4-yl)-methanone (Example 6, step 4) and (2-bromoethyl)-methylether. The desired product was obtained in a yield of 70% as white foam. MS (m/e): 556.3 (M+H, 100%).

Example 15

[6-Bromo-5-(1-isopropyl-piperidin-4-yloxy)-1-(3-methoxy-propyl)-1H-indol-2-yl]-(1,1-dioxo-1λ$^6$-thiomorpholin-4-yl)-methanone In analogy to the procedure described for the synthesis of example 1, step 1, the title compound was synthesized from [6-bromo-5-(1-isopropyl-piperidin-4-yloxy)-1H-indol-2-yl]-(1,1-dioxo-1λ$^6$-thiomorpholin-4-yl)-methanone (Example 6, step 4) and 1-bromo-3-methoxypropane. The desired product was obtained in a yield of 65% as light yellow foam. MS (m/e): 570.4 (M+H, 70%).

Example 16

[6-Bromo-1-(2-hydroxy-ethyl)-5-(1-isopropyl-piperidin-4-yloxy)-1H-indol-2-yl]-(1,1-dioxo-1λ$^6$-thiomorpholin-4-yl)-methanone step 1: [6-Bromo-1-[2-(tert-butyl-dimethyl-silanyloxy)-ethyl]-5-(1-isopropyl-piperidin-4-yloxy)-1H-indol-2-yl]-(1,1-dioxo-1λ$^6$-thiomorpholin-4-yl)-methanone In analogy to the procedure described for the synthesis of example 1, step 1, the title compound was synthesized from [6-bromo-5-(1-isopropyl-piperidin-4-yloxy)-1H-indol-2-yl]-(1,1-dioxo-1λ$^6$-thiomorpholin-4-yl)-methanone (Example 6, step 4) and (2-bromoethoxy)-tert-butyldimethylsilane. The desired product was obtained in a yield of 50% as colorless oil. MS (m/e): 656.4 (M+H, 50%).

step 2: [6-Bromo-1-(2-hydroxy-ethyl)-5-(1-isopropyl-piperidin-4-yloxy)-1H-indol-2-yl]-(1,1-dioxo-1λ$^6$-thiomorpholin-4-yl)-methanone A mixture of [6-bromo-1-[2-(tert-butyl-dimethyl-silanyloxy)-ethyl]-5-(1-isopropyl-piperidin-4-yloxy)-1H-indol-2-yl]-(1,1-dioxo-1λ$^6$-thiomorpholin-4-yl)-methanone (130 mg, 1.0 eq.) and trifluoroacetic acid in dichloromethane was stirred for 1 h at room temperature and concentrated in vacuo. The crude mixture was partitioned between an aqueous solution of sodium hydroxide and dichloromethane. The aqueous layer was extracted with dichloromethane. Combined organic layers were washed with brine, dried over sodium sulfate, filtered and evaporated in vacuo, to yield 106 mg (99%) of the desired product as white foam. MS (m/e): 542.1 (M+H, 100%).

Example 17

[6-Bromo-1-(3-hydroxy-propyl)-5-(1-isopropyl-piperidin-4-yloxy)-1H-indol-2-yl]-(1,1-dioxo-1λ$^6$-thiomorpholin-4-yl)-methanone Step 1: [6-Bromo-1-[3-(tert-butyl-dimethyl-silanyloxy)-propyl]-5-(1-isopropyl-piperidin-4-yloxy)-1H-indol-2-yl]-(1,1-dioxo-1λ$^6$-thiomorpholin-4-yl)-methanone In analogy to the procedure described for the synthesis of example 1, step 1, the title compound was synthesized from [6-bromo-5-(1-isopropyl-piperidin-4-yloxy)-1H-indol-2-yl]-(1,1-dioxo-1λ$^6$-thiomorpholin-4-yl)-methanone (Example 6, step 4) and (3-bromopropoxy)-tert-butyldimethylsilane. The desired product was obtained in a yield of 65% as colorless oil. MS (m/e): 670.5 (M+H, 100%).

Step 2: [6-Bromo-1-(3-hydroxy-propyl)-5-(1-isopropyl-piperidin-4-yloxy)-1H-indol-2-yl]-(1,1-Dioxo-1λ6-thiomorpholin-4-yl)-methanone In analogy to the procedure described for the synthesis of example 16, step 1, the title compound was synthesized from [6-bromo-1-[3-(tert-butyl-dimethyl-silanyloxy)-propyl]-5-(1-isopropyl-piperidin-4-yloxy)-1H-indol-2-yl]-(1,1-dioxo-1λ$^6$-thiomorpholin-4-yl)-methanone (Example 17, step 1). The desired product was obtained in a yield of 99% as a white foam. MS (m/e): 556.5 (M+H, 70%).

Example 18 and 19

(S)-2-[2-(1,1-Dioxo-1λ$^6$-thiomorpholine-4-carbonyl)-5-(1-isopropyl-piperidin-4-yloxy)-indol-1-yl]-propionitrile and (R)-2-[2-(1,1-dioxo-1λ$^6$-thiomorpholine-4-carbonyl)-5-(1-isopropyl-piperidin-4-yloxy)-indol-1-yl]-propionitrile A racemic mixture of rac-2-[2-(1,1-dioxo-1λ$^6$-thiomorpholine-4-carbonyl)-5-(1-isopropyl-piperidin-4-yloxy)-indol-1-yl]-propionitrile (Example 12, 190 mg) in ethanol (8 mL) was resolved by chiral chromatography using a DAICEL Chiralcel OD with Ethanol/heptane 25:75 v:v. 2 fractions of opposite optical rotation were isolated and dried in vacuo.

Fraction 1, negative rotation at 220 nm, 60 mg of a yellow solid, (32%) MS (m/e): 473.5 (MH+, 100%).
Fraction 2, positive rotation at 220 nm, 84 mg of a yellow solid, (44%) MS (m/e): 473.5 (MH+, 100%).

Example 20

[5-(1-Cyclobutyl-piperidin-4-yloxy)-1-isopropyl-1H-indol-2-yl]-(1,1-dioxo-1$\lambda^6$-thiomorpholin-4-yl)-methanone Step 1:
5-Benzyloxy-1-isopropyl-1H-indole-2-carboxylic acid ethyl ester To a mixture of 5-benzyloxyindole-2-carboxylic acid ethyl ester (30 g, 1.0 eq.) and cesium carbonate (58. g, 1.75 eq.) in acetonitrile (200 mL), was added isopropylmethane sulfonate (24.8 g, 1.75 eq.). The reaction mixture was refluxed for 18 h and then concentrated in vacuo. The residue was partitioned between water and methyl-tert-butylether. The aqueous layer was extracted with methyl-tert-butylether and the combined organic layers were washed with brine, dried over sodium sulfate, filtered and dried in vacuo. then purified on silica eluting with dichloromethane/methanol 98:2 v:v. The crude material was purified by crystallization in ethanol and dried in vacuo to yield 31 g (90%) of the desired product as an off-white oil. MS (m/e): 338.4 (MH+, 100%).

Step 2:
5-Benzyloxy-1-isopropyl-1H-indole-2-carboxylic acid

5-Benzyloxy-1-isopropyl-1H-indole-2-carboxylic acid ethyl ester (47.5 g, 1.0 eq.) and lithium hydroxide (6.56 g, 1.1 eq.) in a mixture of tetrahydofuran (360 mL), water (180 mL) and methanol (120 mL) was refluxed for 2 h then the reaction mixture was concentrated in vacuo. The residue was stirred vigorously in aqueous hydrochloric acid (2N, final pH: 2). The white precipitate was filtered, washed with water then dried in vacuo to yield 41.6 g (96%) of the desired product as white oil. MS (m/e): 308.5 (M–H, 100%).

Step 3:
5-Hydroxy-1-isopropyl-1H-indole-2-carboxylic acid

A mixture of 5-benzyloxy-1-isopropyl-1H-indole-2-carboxylic acid (41.6 g, 1.0 eq.) and palladium on activated charcoal (10% m:m, 4.3 g, 0.03 eq.) in ethyl acetate (330 mL) and ethanol (235 mL) was flushed with hydrogen, then vigorously stirred for 2 h30 at room temperature. The resulting back suspension was filtered through a dicalite pad. The pad was washed with a mixture of ethyl acetate and ethanol then the liquor was evaporated in vacuo to yield 26.3 g (quant.) of the desired product as off-white oil. MS (m/e): 218.2 (M–H, 100%).

Step 4: (1,1-Dioxo-1$\lambda^6$-thiomorpholin-4-yl)-(5-hydroxy-1-isopropyl-1H-indol-2-yl)-methanone In analogy to the procedure described for the synthesis of example 1, step 3, the title compound was synthesized from 5-Hydroxy-1-isopropyl-1H-indole-2-carboxylic acid (Example 20, step 3) and thiomorpholine-1,1-dioxide (purchased at Syntec, ref. M1201). The desired product was obtained in a yield of 75% as white solid. MS (m/e): 335.5 (M–H, 100%).

Step 5: 4-[2-(1,1-Dioxo-1$\lambda^6$-thiomorpholine-4-carbonyl)-1-isopropyl-1H-indol-5-yloxy]-piperidine-1-carboxylic acid tert-butyl ester To a cold (0° C.) mixture of (1,1-dioxo-1$\lambda^6$-thiomorpholin-4-yl)-(5-hydroxy-1-isopropyl-1H-indol-2-yl)-methanone (890 mg, 1.0 eq.), 1-tert-butyloxycarbonyl-4-hydroxy-piperidine (659 mg, 1.2 eq.) and triphenylphosphine (858 mg, 1.2 eq.) in tetrahydrofuran (6 mL) was added dropwise a solution of di-tert-butyl-azodicarboxylate (746 mg, 1.0 eq.) in tetrahydrofuran (4 mL). The reaction mixture was stirred for 15 h at room temperature, concentrated in vacuo, then purified on silica eluting with a gradient of cyclohexane/ethyl acetate. One fraction was isolated to yield 434 mg (31.6%) of the desired product as white oil. MS (m/e): 520.7 (MH+, 100%).

Step 6: (1,1-Dioxo-1$\lambda^6$-thiomorpholin-4-yl)-[1-isopropyl-5-(piperidin-4-yloxy)-1H-indol-2-yl]-methanone To a cold (0° C.) mixture of 4-[2-(1,1-dioxo-1$\lambda^6$-thiomorpholine-4-carbonyl)-1-isopropyl-1H-indol-5-yloxy]-piperidine-1-carboxylic acid tert-butyl ester (410 mg, 1.0 eq.) in dichloromethane (8 mL) was added dropwise trifluoroacetic acid (920 mg, 10 eq.). The mixture was stirred overnight at room temperature then concentrated in vacuo. The residue was partitioned between a potassium carbonate aqueous solution and ethyl acetate. The aqueous layer was extracted with ethyl acetate and the combined organic layers were dried over sodium sulfate, filtered and dried in vacuo. The residue was then purified on silica eluting with dichloromethane/methanol/ammoniac 95:5:0.25 v:v:v. to yield 296 mg (86%) of the desired product as off-white oil. MS (m/e): 420.4 (MH+, 100%).

Step 7: [5-(1-Cyclobutyl-piperidin-4-yloxy)-1-isopropyl-1H-indol-2-yl]-(1,1-dioxo-1$\lambda^6$-thiomorpholin-4-yl)-methanone To a mixture of (1,1-dioxo-1$\lambda^6$-thiomorpholin-4-yl)-[1-isopropyl-5-(piperidin-4-yloxy)-1H-indol-2-yl]-methanone (268 mg, 1.0 eq.) in acetic acid (115 mg, 3.0 eq.) was added a solution of cyclobutane (90 mg, 2.0 eq.) in tetrahydrofuran (8 mL). The mixture was stirred for 2 h at 55° C. Then the mixture was cooled to room temperature and sodium triacetoxyborohydride (279 mg, 2.0 eq.) was added. The reaction mixture was stirred overnight at 65° C. The residue was partitioned between water and ethyl acetate. The organic layer was washed with a sodium hydrogenocarbonate aqueous solution, dried over sodium sulfate, filtered and dried in vacuo. Then the residue was purified on silica eluting with a gradient of dichloromethane/methanol to yield 97 mg (32%) of the desired product as off-white oil. MS (m/e): 474.5 (MH+, 100%).

Example 21

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |

| -continued | | |
|---|---|---|
| Ingredients | Per tablet | |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 22

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 23

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 24

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

| -continued | |
|---|---|
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 25

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula I,

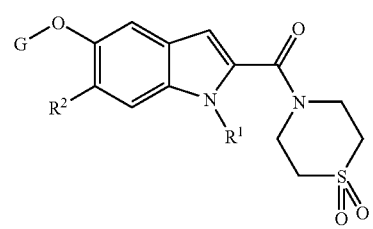

wherein:
$R^1$ is selected from the group consisting of hydrogen, lower alkyl, lower hydroxyalkyl, lower alkoxyalkyl, lower halogenoalkyl, lower cycloalkylalkyl,
lower alkanoyl, lower alkoxycarbonyl, lower cyanoalkyl, lower alkylsulfonyl, phenylsulfonyl wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl;
phenyl unsubstituted or substituted with one or two groups independently selected from lower alkyl, halogen, cyano, lower halogenoalkyl, lower alkoxy, lower halogenoalkoxy and lower hydroxyalkyl;

lower phenylalkyl, wherein the phenyl ring may be unsubstituted or substituted with one or two groups independently selected from lower alkyl, halogen, cyano, lower halogenoalkyl, lower alkoxy, lower halogenoalkoxy and lower hydroxyalkyl; and heteroaryl unsubstituted or substituted with one or two groups independently selected from lower alkyl, lower alkoxy, halogen, lower halogenoalkyl, lower halogenoalkoxy and cyano;

$R^2$ is hydrogen or halogen;

G is a group selected from

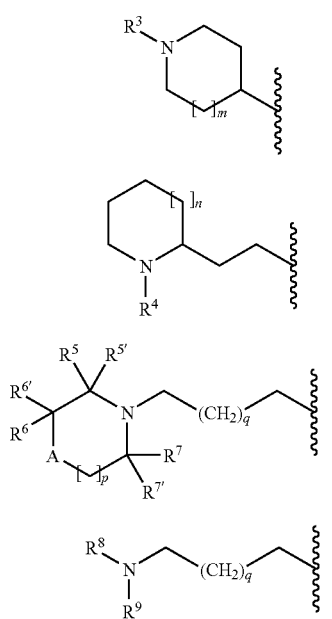

wherein
m is 0, 1 or 2;
$R^3$ is selected from lower alkyl, lower halogenoalkyl, cycloalkyl, halogenocycloalkyl, lower cycloalkylalkyl and lower phenylalkyl;
n is 0, 1 or 2;
$R^4$ is lower alkyl;
p is 0, 1 or 2;
q is 0, 1 or 2;
A is selected from $CR^{10}R^{10'}$, O and S;
$R^5$, $R^{5'}$, $R^6$, $R^{6'}$, $R^7$, $R^{7'}$, $R^{10}$ and $R^{10'}$ independently from each other are selected from the group consisting of hydrogen, lower alkyl, hydoxy, halogen and dialkylamino, or
$R^6$ and $R^{10}$ together form a double bond;
$R^8$ is lower alkyl;
$R^9$ is $C_3$-$C_6$-alkyl;
and pharmaceutically acceptable salts thereof.

2. The compound according to claim 1, wherein $R^1$ is selected from the group consisting of hydrogen, lower alkyl, lower hydroxyalkyl, lower alkoxyalkyl, lower halogenoalkyl, lower cycloalkylalkyl, lower cyanoalkyl,
lower alkylsulfonyl and
phenyl unsubstituted or substituted with one or two groups independently selected from lower alkyl, halogen, cyano, lower halogenoalkyl, lower alkoxy, lower halogenoalkoxy and lower hydroxyalkyl.

3. The compound according to claim 1, wherein $R^1$ is selected from the group consisting of hydrogen, lower alkyl and lower halogenoalkyl.

4. The compound according to claim 1, wherein $R^1$ is hydrogen.

5. The compound according to claim 1, wherein $R^1$ is lower halogenoalkyl.

6. The compound according to claim 1, wherein $R^1$ is lower cyanoalkyl.

7. The compound according to claim 1, wherein $R^1$ is heteroaryl unsubstituted or substituted with one or two groups independently selected from lower alkyl, lower alkoxy, halogen, lower halogenoalkyl, lower halogenoalkoxy and cyano.

8. The compound according to claim 1, wherein $R^2$ is hydrogen.

9. The compound according to claim 1, wherein $R^2$ is halogen.

10. The compound according to claim 1, wherein G signifies

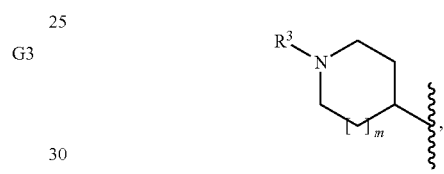

wherein m is 0, 1 or 2 and $R^3$ is selected from lower alkyl, cycloalkyl, lower cycloalkylalkyl and lower phenylalkyl.

11. The compound according to claim 1, wherein m is 0 or 1 and $R^3$ is lower alkyl.

12. The compound according to claim 11, wherein $R^3$ is isopropyl.

13. The compound according to claim 1, wherein G signifies

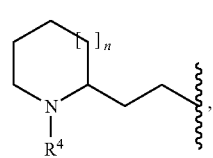

wherein n is 0, 1 or 2 and $R^4$ is lower alkyl.

14. The compound according to claim 1, wherein G signifies

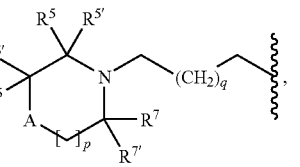

wherein p is 0, 1 or 2; q is 0, 1 or 2; A is selected from $CR^{10}R^{10'}$, O and S; and R$^5$, R$^{5'}$, R$^6$, R$^{6'}$, R$^7$, R$^{7'}$, R$^{10}$ and R$^{10'}$ independently from each other are selected from the group consisting of hydrogen, lower alkyl, hydoxy, halogen and dialkylamino, or R$^6$ and R$^{10}$ together form a double bond.

15. The compound according to claim 1, wherein G signifies

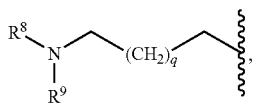

G4 wherein q is 0, 1 or 2, R$^8$ is lower alkyl and R$^9$ is lower alkyl.

16. The compound according to claim 1, selected from the group consisting of
- (1,1-dioxo-thiomorpholin-4-yl)-[5-(1-isopropyl-piperidin-4-yloxy)-1-(2,2,2-trifluoro-ethyl)-1H-indol-2-yl]-methanone,
- (1,1-dioxo-thiomorpholin-4-yl)-[5-(1-isopropyl-piperidin-4-yloxy)-1H-indol-2-yl]-methanone,
- (1,1-dioxo-thiomorpholin-4-yl)-[1-isopropyl-5-(1-isopropyl-piperidin-4-yloxy)-1H-indol-2-yl]-methanone,
- (1,1-dioxo-thiomorpholin-4-yl)-[5-(1-isopropyl-pyrrolidin-3S-yloxy)-1H-indol-2-yl]-methanone, and pharmaceutically acceptable salts thereof.

17. The compound according to claim 1, selected from the group consisting of
- 5-[2-(1,1-dioxo-1λ$^6$-thiomorpholine-4-carbonyl)-5-(1-isopropyl-piperidin-4-yloxy)-indol-1-yl]-pyridine-2-carbonitrile,
- [6-bromo-5-(1-isopropyl-piperidin-4-yloxy)-1H-indol-2-yl]-(1,1-dioxo-1λ$^6$-thiomorpholin-4-yl)-methanone,
- [6-bromo-1-isopropyl-5-(1-isopropyl-piperidin-4-yloxy)-1H-indol-2-yl]-(1,1-dioxo-1λ$^6$-thiomorpholin-4-yl)-methanone,
- [6-bromo-5-(1-isopropyl-piperidin-4-yloxy)-1-(2,2,2-trifluoro-ethyl)-1H-indol-2-yl]-(1,1-dioxo-1λ$^6$-thiomorpholin-4-yl)-methanone,
- [6-bromo-1-(2-chloro-pyridin-4-yl)-5-(1-isopropyl-piperidin-4-yloxy)-1H-indol-2-yl]-(1,1-dioxo-1λ$^6$-thiomorpholin-4-yl)-methanone,
- (1,1-dioxo-1λ$^6$-thiomorpholin-4-yl)-[5-(1-isopropyl-piperidin-4-yloxy)-1-(3-trifluoromethyl-phenyl)-1H-indol-2-yl]-methanone,
- [1-(2-chloro-pyridin-4-yl)-5-(1-isopropyl-piperidin-4-yloxy)-1H-indol-2-yl]-(1,1-dioxo-1λ$^6$-thiomorpholin-4-yl)-methanone,
- 2-[2-(1,1-dioxo-1λ$^6$-thiomorpholine-4-carbonyl)-5-(1-isopropyl-piperidin-4-yloxy)-indol-1-yl]-propionitrile,
- (1,1-dioxo-1λ$^6$-thiomorpholin-4-yl)-[5-(1-isopropyl-piperidin-4-yloxy)-1-pyrimidin-5-yl-1H-indol-2-yl]-methanone,
- [6-bromo-5-(1-isopropyl-piperidin-4-yloxy)-1-(2-methoxy-ethyl)-1H-indol-2-yl]-(1,1-dioxo-1λ$^6$-thiomorpholin-4-yl)-methanone,
- [6-bromo-5-(1-isopropyl-piperidin-4-yloxy)-1-(3-methoxy-propyl)-1H-indol-2-yl]-(1,1-dioxo-1λ$^6$-thiomorpholin-4-yl)-methanone,
- [6-bromo-1-(2-hydroxy-ethyl)-5-(1-isopropyl-piperidin-4-yloxy)-1H-indol-2-yl]-(1,1-dioxo-1λ$^6$-thiomorpholin-4-yl)-methanone,
- [6-bromo-1-(3-hydroxy-propyl)-5-(1-isopropyl-piperidin-4-yloxy)-1H-indol-2-yl]-(1,1-Dioxo-1λ$^6$-thiomorpholin-4-yl)-methanone,
- (S)-2-[2-(1,1-dioxo-1λ$^6$-thiomorpholine-4-carbonyl)-5-(1-isopropyl-piperidin-4-yloxy)-indol-1-yl]-propionitrile,
- (R)-2-[2-(1,1-dioxo-1λ$^6$-thiomorpholine-4-carbonyl)-5-(1-isopropyl-piperidin-4-yloxy)-indol-1-yl]-propionitrile,
- [5-(1-cyclobutyl-piperidin-4-yloxy)-1-isopropyl-1H-indol-2-yl]-(1,1-dioxo-1λ$^6$-thiomorpholin-4-yl)-methanone, and pharmaceutically acceptable salts thereof.

18. A process for the manufacture of compounds according to claim 1, comprising the step of:
reacting a compound of formula II

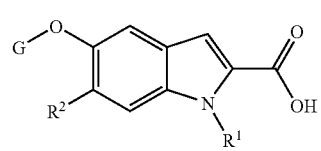

II or a salt thereof,
wherein R$^1$ and R$^2$ are as defined in claim 1,
with the amine of the formula III

III to obtain a compound of the formula I

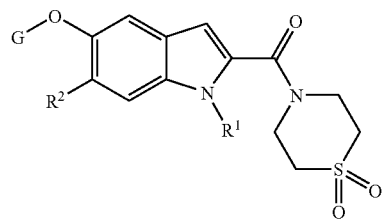

I wherein R$^1$, R$^2$ and G are as defined in claim 1,
and if desired,
converting the compound obtained into a pharmaceutically acceptable acid addition salt.

19. A pharmaceutical composition, comprising a therapeutically effective amount of a compound according to claim 1 as well as a pharmaceutically acceptable carrier and/or adjuvant.

* * * * *